US 9,386,865 B2

(12) United States Patent
Bally (10) Patent No.: US 9,386,865 B2
(45) Date of Patent: Jul. 12, 2016

(54) STORAGE BIN SYSTEM

(71) Applicant: Nexxspan Healthcare, LLC, Lithia, FL (US)

(72) Inventor: Alexander Bally, Marston Mills, MA (US)

(73) Assignee: Nexxspan Healthcare, LLC, Lithia, FL (US)

( * ) Notice: Subject to any disclaimer, the term of this patent is extended or adjusted under 35 U.S.C. 154(b) by 0 days.

(21) Appl. No.: 14/541,983

(22) Filed: Nov. 14, 2014

(65) Prior Publication Data

US 2015/0136719 A1    May 21, 2015

Related U.S. Application Data

(60) Provisional application No. 61/905,593, filed on Nov. 18, 2013.

(51) Int. Cl.
| | |
|---|---|
| A47F 5/08 | (2006.01) |
| A47F 3/14 | (2006.01) |
| A47F 5/00 | (2006.01) |
| A61B 19/02 | (2006.01) |

(52) U.S. Cl.
CPC .............. *A47F 3/14* (2013.01); *A61B 19/0271* (2013.01); *A47F 5/00* (2013.01); *A47F 5/08* (2013.01); *A61B 19/0256* (2013.01); *A61B 2019/0275* (2013.01); *A61B 2019/0278* (2013.01); *A61B 2019/0281* (2013.01); *A61B 2050/3006* (2016.02); *A61B 2050/3011* (2016.02); *A61G 2203/78* (2013.01)

(58) Field of Classification Search
CPC .............. A47F 3/14; A47F 5/00; A47F 5/08; A61B 19/0271; A61B 19/0256; A61B 2019/0275; A61B 2019/0278; A61B 2019/0281; A61B 2050/3006; A61B 2050/3011; A61G 2203/78
USPC ................. 211/126.7, 126.12, 126.16, 88.01, 211/94.01, 90.01–90.04, 126.1–126.5, 211/126.11; 220/23.88, 23.86, 480, 481, 220/482, 476, 23.2, 23.83; 108/108, 108/147.11, 147.17
See application file for complete search history.

(56) References Cited

U.S. PATENT DOCUMENTS

| | | | | | |
|---|---|---|---|---|---|
| 144,343 | A | * | 11/1873 | Martin | ..................... 220/592.15 |
| 613,231 | A | * | 11/1898 | Bennett | ...................... 211/88.01 |
| 1,221,789 | A | * | 4/1917 | Brown | .......................... 206/515 |
| 2,534,793 | A | * | 12/1950 | Olson | ................................ 4/658 |
| 2,614,399 | A | * | 10/1952 | Roethel | ......................... 249/120 |
| 2,702,649 | A | * | 2/1955 | Neilson | .......................... 220/482 |
| 2,704,974 | A | * | 3/1955 | Steman | ............................ 99/422 |

(Continued)

OTHER PUBLICATIONS

Bally, Alexander; PCT Application entitled: Storage Bin System having serial No. PCT/US14/65743, filed Nov. 14, 2014, 32 pgs.

(Continued)

*Primary Examiner* — Joshua J Michener
*Assistant Examiner* — Devin Barnett
(74) *Attorney, Agent, or Firm* — Taylor English Duma LLP (57) ABSTRACT

Disclosed is a storage bin apparatus including a bin support, the bin support including a bottom panel and a front stop; and a mounting adapter, the mounting adapter attached to the bin support at a connection point and extending from the connection point away from the front stop, the mounting adapter mountable to a mounting member. Also disclosed is a storage bin system including a bin support, the bin support including a bottom panel and a front stop; and a bin.

16 Claims, 9 Drawing Sheets

(56) References Cited

U.S. PATENT DOCUMENTS

| | | | | |
|---|---|---|---|---|
| 2,770,513 A * | 11/1956 | Brown | | 220/482 |
| 2,891,678 A * | 6/1959 | Levy | | A47F 5/0025 |
| | | | | 211/133.6 |
| 2,901,120 A * | 8/1959 | Abrahamson | | 211/126.12 |
| 2,914,189 A * | 11/1959 | Bishop et al. | | 211/129.1 |
| 2,944,694 A * | 7/1960 | Kinsey | | 206/541 |
| 2,982,423 A * | 5/1961 | Handler et al. | | 211/126.1 |
| 3,097,746 A * | 7/1963 | Handler et al. | | 211/133.3 |
| 3,101,864 A * | 8/1963 | Glickman | | 206/557 |
| 3,187,924 A * | 6/1965 | Marcus | | 220/480 |
| 3,241,706 A * | 3/1966 | Monaco et al. | | 206/558 |
| 3,269,556 A * | 8/1966 | Streater | | 211/132.1 |
| 3,294,351 A * | 12/1966 | Rollins, Jr. | | A47B 96/028 |
| | | | | 211/90.03 |
| 3,299,839 A * | 1/1967 | Nordbak | | 108/152 |
| 3,498,494 A * | 3/1970 | Voorhees, Jr. | | 206/501 |
| 3,589,554 A * | 6/1971 | Smith | | 220/23.83 |
| 3,647,078 A * | 3/1972 | Fortunato | | 211/134 |
| 3,661,271 A * | 5/1972 | Fisher et al. | | 211/88.01 |
| 3,710,900 A * | 1/1973 | Fink | | 206/387.15 |
| 3,729,113 A * | 4/1973 | Lopatka | | 220/480 |
| 3,752,323 A * | 8/1973 | Kayden | | 211/86.01 |
| D229,894 S * | 1/1974 | Reifers | | D9/425 |
| 3,811,560 A * | 5/1974 | Schilling et al. | | 220/521 |
| 3,840,990 A * | 10/1974 | Laurenti | | 30/341 |
| 3,886,698 A * | 6/1975 | Raith et al. | | 52/36.4 |
| 4,040,588 A * | 8/1977 | Papsco et al. | | 248/245 |
| 4,109,797 A * | 8/1978 | Brunette | | 211/133.5 |
| 4,122,955 A * | 10/1978 | Celms | | 211/133.5 |
| 4,131,203 A * | 12/1978 | Bridges | | 211/88.01 |
| 4,151,917 A * | 5/1979 | Pugh | | 211/88.01 |
| 4,155,459 A * | 5/1979 | Marschak | | 211/49.1 |
| 4,228,906 A * | 10/1980 | Jones | | 211/88.01 |
| D260,345 S * | 8/1981 | Goodrich | | D7/548 |
| 4,349,113 A * | 9/1982 | Schreiner | | 211/103 |
| 4,377,241 A * | 3/1983 | Schreiner | | 211/133.3 |
| 4,401,222 A * | 8/1983 | Kulikowski et al. | | 211/94.01 |
| 4,429,850 A * | 2/1984 | Weber et al. | | 248/250 |
| 4,498,693 A * | 2/1985 | Schindele | | A61G 13/107 |
| | | | | 248/223.41 |
| 4,592,286 A * | 6/1986 | Trubiano | | 108/108 |
| 4,646,921 A * | 3/1987 | Canter | | 211/126.1 |
| 4,687,094 A * | 8/1987 | Allsop et al. | | 206/774 |
| 4,765,492 A * | 8/1988 | Howard et al. | | 211/55 |
| 4,807,659 A * | 2/1989 | Schindele | | F16L 3/01 |
| | | | | 137/271 |
| 4,828,121 A * | 5/1989 | Willcocks, Jr. | | A47F 5/0068 |
| | | | | 211/126.1 |
| 4,869,378 A * | 9/1989 | Miller | | A47F 5/0853 |
| | | | | 211/62 |
| 5,022,537 A * | 6/1991 | Henriquez | | A47F 5/0807 |
| | | | | 211/88.01 |
| 5,038,689 A * | 8/1991 | Duffy | | 108/108 |
| D342,364 S * | 12/1993 | Hobson | | D3/313 |
| 5,358,692 A * | 10/1994 | Reynolds | | 422/536 |
| D358,765 S * | 5/1995 | Dickinson et al. | | D3/279 |
| 5,417,396 A * | 5/1995 | Merl | | 248/222.14 |
| 5,441,707 A * | 8/1995 | Lewis et al. | | 422/300 |
| 5,447,237 A | 9/1995 | Carter et al. | | |
| 5,549,379 A * | 8/1996 | Jun et al. | | 312/408 |
| 5,564,805 A | 10/1996 | Dickson | | |
| 5,575,444 A * | 11/1996 | Otema | | 248/242 |
| D392,804 S * | 3/1998 | Wilkening et al. | | D3/313 |
| 5,899,345 A * | 5/1999 | Fuller et al. | | 211/132.1 |
| 5,913,584 A * | 6/1999 | Swindell et al. | | 312/408 |
| 5,921,411 A * | 7/1999 | Merl | | 211/90.01 |
| 5,975,318 A * | 11/1999 | Jay | | 211/90.01 |
| 6,076,904 A * | 6/2000 | Shepherd et al. | | 312/209 |
| 6,168,032 B1 * | 1/2001 | Merl | | 211/59.2 |
| 6,189,705 B1 * | 2/2001 | Saylor et al. | | 211/11 |
| 6,394,297 B1 * | 5/2002 | Nance | | 220/23.4 |
| 6,471,080 B1 * | 10/2002 | Hoffmann | | 211/126.1 |
| 6,502,733 B1 * | 1/2003 | Gebhardt et al. | | 220/23.86 |
| D487,193 S * | 3/2004 | Liu | | D3/313 |
| 6,793,070 B2 * | 9/2004 | Dye | | 206/45.24 |
| 6,999,306 B2 * | 2/2006 | Walczak et al. | | 361/679.37 |
| 7,428,972 B2 * | 9/2008 | Warner et al. | | 211/59.1 |
| 7,530,329 B1 * | 5/2009 | Paris et al. | | 119/61.57 |
| D600,502 S * | 9/2009 | Paslawski | | D7/548 |
| 7,611,111 B2 * | 11/2009 | Costa et al. | | 248/243 |
| D620,761 S * | 8/2010 | Boudreau | | D7/549 |
| 8,016,131 B2 * | 9/2011 | Belokin et al. | | 211/75 |
| 8,042,700 B1 * | 10/2011 | Smalley | | 211/90.01 |
| 8,061,539 B2 * | 11/2011 | Punzel et al. | | 211/103 |
| D658,417 S * | 5/2012 | Kusmer et al. | | D6/567 |
| 8,177,311 B2 * | 5/2012 | Apgood, II | | A47B 57/34 |
| | | | | 312/245 |
| 8,210,372 B2 * | 7/2012 | Visser | | 211/126.7 |
| 8,517,320 B1 * | 8/2013 | Nicely | | 248/223.41 |
| 8,672,161 B2 * | 3/2014 | Apps | | 220/23.88 |
| 2001/0045403 A1 * | 11/2001 | Robertson | | 211/59.2 |
| 2004/0011752 A1 * | 1/2004 | Zadak | | 211/90.03 |
| 2004/0149182 A1 * | 8/2004 | Bienick et al. | | 108/108 |
| 2004/0211736 A1 * | 10/2004 | Mason | | 211/59.2 |
| 2006/0138133 A1 * | 6/2006 | Holland | | 220/23.86 |
| 2006/0175326 A1 * | 8/2006 | Kirkland et al. | | 220/4.21 |
| 2006/0180561 A1 * | 8/2006 | Wisnoski et al. | | 211/94.01 |
| 2006/0254481 A1 * | 11/2006 | Lee et al. | | 108/108 |
| 2007/0046160 A1 * | 3/2007 | Egan | | 312/408 |
| 2007/0103892 A1 | 5/2007 | McDaniel et al. | | |
| 2007/0221103 A1 * | 9/2007 | Trausch | | 108/108 |
| 2007/0295681 A1 * | 12/2007 | Colin | | 211/90.03 |
| 2008/0099279 A1 | 5/2008 | Griswold et al. | | |
| 2008/0302744 A1 * | 12/2008 | Rosenberg | | 211/94.01 |
| 2009/0038983 A1 | 2/2009 | Kieffer | | |
| 2010/0044328 A1 * | 2/2010 | Barkdoll et al. | | 211/88.01 |
| 2010/0283368 A1 * | 11/2010 | Lee | | F25D 23/04 |
| | | | | 312/405.1 |
| 2011/0084040 A1 * | 4/2011 | Curtin | | 211/126.7 |
| 2011/0278196 A1 | 11/2011 | Hamilton | | |
| 2011/0278245 A1 * | 11/2011 | Noble Colin | | 211/59.2 |
| 2013/0199963 A1 | 8/2013 | Garfinkle | | |
| 2014/0205371 A1 * | 7/2014 | Bally | | A61G 12/008 |
| | | | | 403/327 |
| 2014/0238991 A1 * | 8/2014 | Morrell | | 220/482 |

OTHER PUBLICATIONS

Bally, Alexander; U.S. Provisional Patent Application Entitled: Modular Storage Bin System having U.S. Appl. No. 61/905,593, filed Nov. 18, 2013; 7 pgs.

Bally, Alexander; International Search Report and Written Opinion for serial No. PCT/US14/65743, filed Nov. 14, 2014, mailed Feb. 11, 2015, 9 pgs.

Bally, Alexander; International Preliminary Report on Patentability for serial No. PCT/US14/65743, filed Nov. 14, 2014, mailed Jun. 2, 2016, 8 pgs.

\* cited by examiner

STORAGE BIN SYSTEM

REFERENCE TO RELATED APPLICATIONS

This application claims priority to U.S. Provisional Application No. 61/905,593, filed Nov. 18, 2013, which is hereby specifically incorporated by reference herein in its entirety.

TECHNICAL FIELD

This disclosure relates generally to storage systems. More specifically, this disclosure relates to support for storage bins that interfaces with a hospital rail system in a manner that improves both functionality and aesthetic appeal.

BACKGROUND

In the daily care of critically ill patients, a great diversity of medical equipment, including infusion management equipment and supplies, pressure transducers, physiological monitors, and other equipment is employed. Such equipment is typically set up at the patient's bedside where the equipment is supported by various stands, racks or hangers. For example, the equipment may be supported by five-star floor stands, it may be attached to headwalls, or it may be suspended from booms that are affixed to the ceiling, floor, wall, column, or wall-mounted columns. The equipment may also be supported or on other stationary or mobile platforms or structures.

All of the equipment needed and supported around hospital rooms also sometimes requires a variety of items such as the following: accessories, tubing, spare parts, replacement sterile components, and patient charts. These components also require a storage location in the room near the equipment together with which these items are being used. Such storage has traditionally been a wire mesh basket that is hung on a wall or by a patient bedside.

The problem with the currently known storage baskets are as follows. The wire mesh from which the baskets are made is difficult to clean. There are too many openings and intersecting corners in these basket designs. As a result, even if the basket is disinfected with a cloth, each wire junction accumulates debris and such. The openings also let smaller items fall through.

Further, the construction of the baskets and their supports are all welded wire, making the structural stability of the baskets relatively low. The baskets are level when newly installed, but as they age, they get bent a little (as they always seem to do) and they look out of whack as they droop. The divider partitions within the baskets are also flimsy. Further, because the individual adapters near each end are attached to a flimsy structure, they are very difficult to handle or attach and remove from the structures to which they are attached because one tends to torque the basket during handling, which can cause the adapters to become misaligned.

Finally, shorter employees cannot see into the baskets if they are high and the contents are difficult to reach. While if a nurse wants to empty out as particular compartment, she or he has to dig into the basked and individually remove the items. There is a need for a sturdy and stable storage system that allows improved access and accessibility to maintain a clean and organized patient care environment.

SUMMARY

Disclosed is a storage bin apparatus including a bin support, the bin support including a bottom panel and a front stop; and a mounting adapter, the mounting adapter attached to the bin support at a connection point and extending from the connection point away from the front stop, the mounting adapter mountable to a mounting member.

Also disclosed is a storage bin system including a bin support, the bin support including a bottom panel and a front stop; and a bin.

Also disclosed is a method of using a storage bin system including mounting a bin support on a structure by attaching a mounting adapter of the bin support to the structure; and placing a bin on the bin support.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

DETAILED DESCRIPTION

Disclosed is a storage bin system and associated methods, systems, devices, and various apparatuses. The storage bin system includes a bin support. In various embodiments, storage bin system includes a mounting adapter such as a rail adapter, a bin, a rail, or other components. It would be understood by one of skill in the art that the disclosed storage bin system is described in but a few exemplary embodiments among many. No particular terminology or description should be considered limiting on the disclosure or the scope of any claims issuing therefrom.

Figure 1:
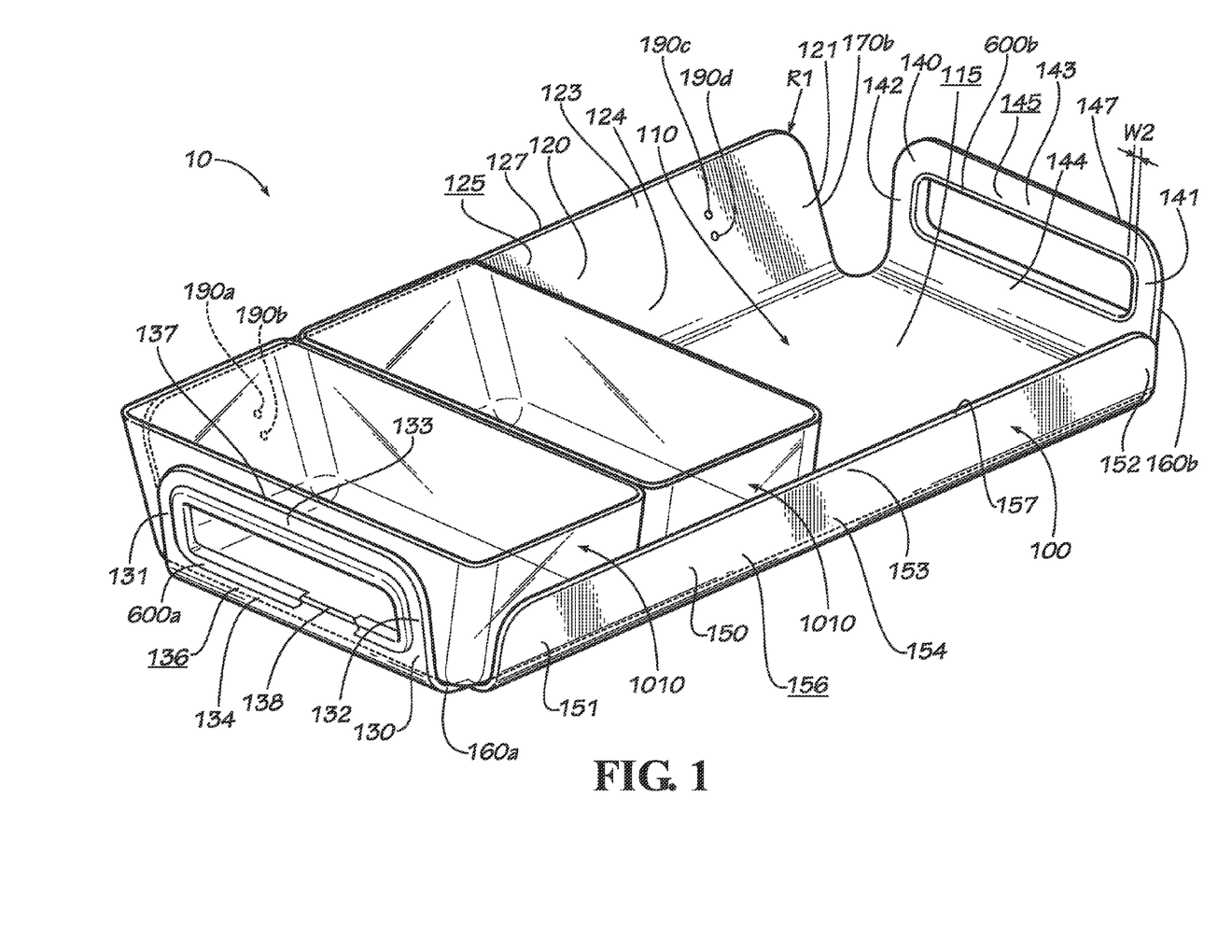
FIG. 1 is a perspective view of one embodiment of a storage bin system.

One embodiment of a storage bin system 10 is disclosed and described in FIG. 1. In various embodiments, the storage bin system 10 includes a bin support 100, rail adapters 400 (shown in FIG. 2) are mounting adapters attachable to a mounting member such as a rail embodied in rail member 500 (shown in FIG. 5), and storage bins identified as bins 1010. In various embodiments, bin support 100 is a tray 100. Storage bin system 10 also may include fasteners 101 in various embodiments to connect rail adapters 400 to bin support 100. Rail adapters 400 are a type of mounting adapters 400. Fasteners 101 may be selected from a group including, but not limited to, screws, bolts, rivets, welds, and various adhesives. Bin support 100 includes a bottom panel 110 which defines an inside surface 115 and an outside surface 116 (shown in FIG. 2). In various embodiments, bin support 100 also includes a rear wall 120, a first side wall 130, a second side wall 140, a front stop 150, and handle inserts 600a,b (600a shown partially cut away for clarity). In various embodiments, front stop 150 is also front wall 150.

In various embodiments, bin support 100 is formed from a blank of material measuring ⅛ inch thick. In various embodiments, bin support 100 may be made from material that has a thickness greater or less than ⅛ inch and the disclosure of a thickness of ⅛ inch should not be considered limiting on the current disclosure. In various embodiments, the bin support 100 could be made from aluminum, steel (including stainless steel), plastics, various composite materials, or other suitable materials. In various embodiments, the material is safe for a magnetic-resonance (MR) or magnetic-resonance-imaging (MRI) environment, meaning that the bin support 100 uses one or more materials from a group of MR-safe or MRI-safe materials including but not limited to aluminum, non-ferrous stainless steel and various other non-ferrous metals, various polymers, and composites. In various embodiments, bin support 100 receives a finish from one or more of a group of finishing materials and methods including, but not limited to, anodizing, powder coating, and painting. In various embodiments, the finish is not visible to the naked eye.

In various embodiments, bottom panel 110 is substantially rectangular in shape and therefore has four ends or sides. Bins 1010 (identified in other embodiments as bins 810,910,1110) are also of a rectangular shape in various embodiments as viewed from the top or from the bottom of the bins 1010, although the disclosure of bins 1010 having a rectangular shape should not be considered limiting on the current disclosure. In various embodiments when viewed from the top or from the bottom, bins 1010 are circular in shape or are otherwise not rectangular in shape. In various other embodiments, bottom panel 110 is not rectangular in shape but instead has a shape other than that of a rectangle to accommodate storage bins of different sizes and shapes inside tray 100.

Figure 10:
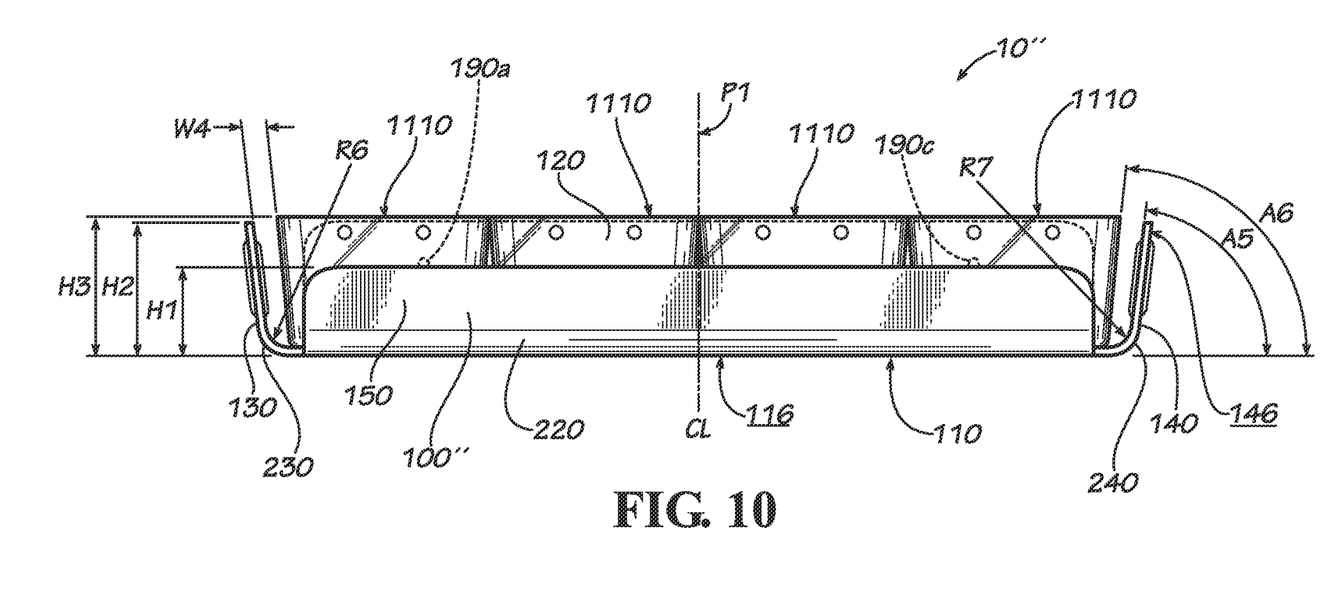
FIG. 10 is a front view of another embodiment of a storage bin system.

Rear wall 120 includes a first end 121, a second end 122 (shown in FIG. 3), a top end 123, and a bottom end 124. In addition, rear wall 120 defines an inside surface 125, an outside surface 126 (shown in FIG. 3), an edge 127, and a plurality of mounting holes 190a,b,c,d for mounting rail adapters 400a,b to rear wall 120. In various embodiments, mounting holes 190a,b,c,d are circular in shape and are defined through the entire thickness of rear wall 120 (including inside surface 125 and outside surface 126). In various other embodiments, mounting holes 190a,b,c,d are not circular in shape or are not present at all. In various embodiments, mounting holes 190a,b,c,d serve as a connection point. In various embodiments, rear wall 120 or a portion or surface thereof serves as the connection point. The first side wall 130 includes a first end 131, a second end 132, a top end 133, and a bottom end 134. In addition, the first side wall 130 defines an inside surface 135 (shown in FIG. 7), an outside surface 136, an edge 137, and a hand hold such as a handle cutout 138. The second side wall 140 includes a first end 141, a second end 142, a top end 143, and a bottom end 144. In addition, the second side wall 140 defines an inside surface 145, an outside surface 146 (shown in FIG. 10), an edge 147, and a hand hold such as a handle cutout 148. In various embodiments, the first side wall 130 and the second side wall 140 are mirror images of each other, symmetrical at least about a vertical plane P1 passing through the center of bin support 100 as shown in FIG. 10. In various embodiments, a first half of bin support 100 is a mirror image of a second half of bin support 100 about a vertical plane P1 passing through the center of bin support 100. In various other embodiments, bin support 100 is not symmetrical about vertical plane P1 or any other plane. In various embodiments, the hand hold is embodied by an addition bend, formed flange, or other feature in first side wall 130 or second side wall 140. In various embodiments, the additional bend or other feature in various embodiments includes geometry under which fingers or entire hands may provide support.

In various embodiments, the bin support 10 includes a front stop in the form of front wall 150 in the current embodiment. In various embodiments, the bin support 10 may include a different front stop, such as a raised lip or a plurality of spaced posts. Front wall 150 includes a first end 151, a second end 152, a top end 153, and a bottom end 154. In addition, the front wall 150 defines an inside surface 155 (shown in FIG. 2), an outside surface 156, and an edge 157. In various embodiments, the first side wall 130, the bottom panel 110, and the front wall 150 define a cutout 160a at a front corner of the bin support 100. In various embodiments, the second side wall 140, the bottom panel 110, and the front wall 150 define a cutout 160b at an opposite front corner of the bin support 100. In various embodiments, the first side wall 130, the bottom panel 110, and the rear wall 120 define cutout 170a (shown in FIG. 2), while in various embodiments the second side wall 140, the bottom panel 110, and the rear wall 120 define cutout 170b. In various embodiments, rear wall 120, first side wall 130, second side wall 140, and front wall 150 define edges 127,137,147,157 as having a radius R1 in one or more areas to improve the safety, cleanability, or aesthetic characteristics of bin support 100. Additionally, the vertical edges of cutouts 160a,b and cutouts 170a,b lie in planes that are each orthogonal to inside surface 115 of bottom panel 110 in various embodiments (shown in FIG. 2). In various embodiments, cutouts 160a,b and cutouts 170a,b extend far enough inward from corners of the bin support so as to clear rear radius R4 (shown in FIG. 2), front radius R5 (shown in FIG. 2), and side radii R6,R7 (shown in FIG. 10).

Besides improving the manufacturability of bin support 100 in various embodiments, leaving the corners of bin support 100 open in this way and particular at cutouts 160a,b allows for a user to easily gain access to every part of the inside surfaces of bin support 100. In various embodiments, however, cutouts 170a,b are not present so as to allow edge 127 of rear wall 120 to join with edge 137 of the first side wall 130 and with edge 147 of the second side wall 140, providing extra rigidity to bin support 100 in various embodiments. With the corners cut away, a user is particularly able to easily clean the inside surfaces and corners of bin support 100 because no corner crevices exist in which dirt or liquids are able to be easily trapped and the lowest part of each radius R4,R5,R6,R7 extends to at least one end of each wall of bin support 100 and therefore allows liquids or dirt and the like to be effectively swiped or brushed from the bin support 100.

Moreover, radii R4,R5,R6,R7 are large enough in various embodiments to optimize access with cleaning equipment. In various embodiments, radii R4,R5,R6,R7 measures a minimum of ¼ inch, though the disclosure of ¼ inch should not be considered limiting on the current disclosure. In various other embodiments, radii R4,R5,R6,R7 measures more than ¼ inch. In various other embodiments, radii R4,R5,R6,R7 measures between ⅜ inch and ½ inch. In various other embodiments, radii R4,R5,R6,R7 measures less than ¼ inch. In addition, radii R1,R4,R5,R6,R7 could each have different radius dimensions or may all have the same radius dimension.

Figure 2:
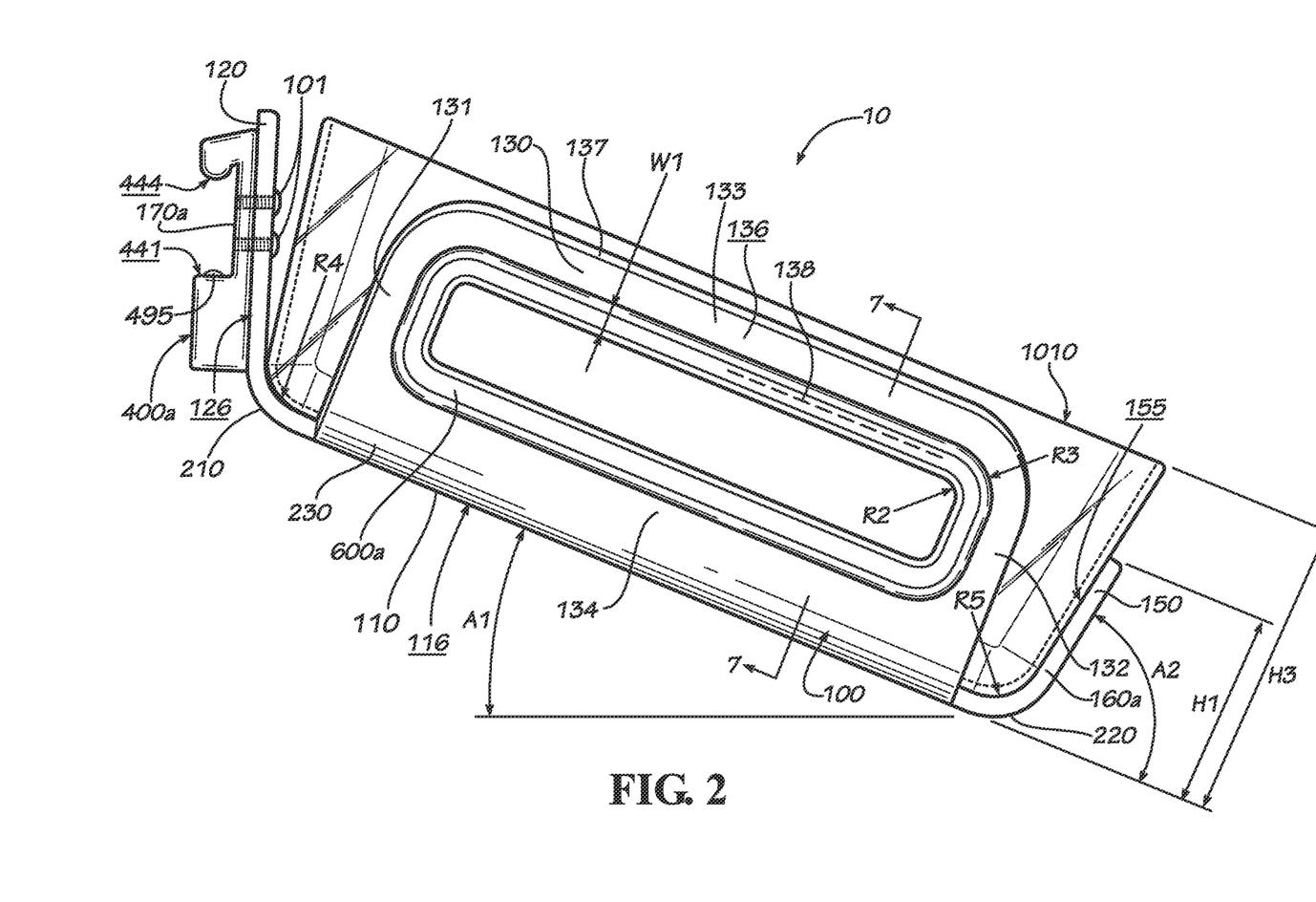
FIG. 2 is a side view of the storage bin system of FIG. 1 including an embodiment of a handle insert.

FIG. 2 is a side view of the storage bin system 10 that further discloses transition portion 210 defined between bottom panel 110 and rear wall 120, transition portion 220 defined between bottom panel 110 and front wall 150, and transition portion 230 defined between bottom panel 110 and first side wall 130. Also disclosed is rail adapter 400a attached to rear wall 120 at outside surface 126 of rear wall 120. Front wall 150 is shown having height H1. Together with bin 1010, storage bin system 10 is shown having overall height H3. In various embodiments, height H1 is less than overall height H3. In various other embodiments, height H1 is more than or equal to overall height H3.

Disclosed inclination angle A1 represents the angle between bottom panel 110 and a horizontal plane. Including in embodiments where the thickness of bottom panel 110 is not constant, inclination angle A1 represents the angle between outside surface 116 of bottom panel 110 and the same horizontal plane. In the current embodiment, inclination angle A1 is approximately twenty degrees. In various embodiments, inclination angle A1 is greater than or less than twenty degrees and the disclosure of twenty degrees should not be considered limiting on the current disclosure. In various embodiments, the inclination angle A1 is zero. When inclination angle A1 is greater than zero in various embodiments, the front of bin support 100 is inclined downward towards the front of bin support 100. When the front of bin support 100 is inclined downward towards the front of bin support 100, greater visibility to the contents of bin 1010 is possible. In various embodiments, incorporating inclination angle A1 facilitates easier access to the storage bin system 10 as a whole because the front of storage bin system 10 is closer to the floor as a result of the inclination angle A1 compared to a bin support 100 that is not so inclined. In various embodiments, inclination angle A1 is set so as to facilitate display and monitoring of the contents of the bins 1010 from across a room and to facilitate physically reaching the storage bin system 10, bins 1010, or the contents thereof.

Disclosed angle A2 represents the angle between front wall 150 and a reference plane defined by outside surface 116 of bottom panel 110. In the current embodiment, angle A2 is approximately eighty degrees. In various embodiments, angle A2 is greater than or less than eighty degrees and the disclosure of eighty degrees should not be considered limiting on the current disclosure. In various embodiments, angle A2 matches the draft angle of bin 1010 held by bin support 100, resulting in a wall of bin 1010 being substantially parallel with front wall 150.

In various embodiments where a right angle is desired between bottom panel 110 and front wall 150, angle A2 is ninety degrees. In various embodiments where a radiused bottom edge of a bin 1010 has a smaller radius than radii such as radius R4 between bottom panel 110 and rear wall 120 or radius R5 between bottom panel 110 and front wall 150, angle A2 may be greater so that only the edge 157 of front wall 150 comes into contact with bin 1010. In various embodiments, selecting angle A2 such that edge 157 of front wall 150 comes into contact with bin 1010 prevents bin 1010 from "riding up" on a large radius R5 between the front wall 150 and the bottom panel 110.

In various embodiments where a slight bend on front wall 150 with respect to bottom panel 110 is desired, angle A2 is close to zero degrees. In various embodiments where no bend at all is required or desired—effectively making front wall 150 and bottom panel 110 coplanar or eliminating front wall 150 entirely in various embodiments, angle A2 is zero degrees or has a negative value such that front wall 150 is bent down instead of bent up. In various embodiments where a front wall (not shown) is coplanar with bottom panel 110 or is bent down so that angle A2 has a negative value, bin 1010 is able to be removed from bin support 100 without lifting bin 1010 away from bottom panel 110 because lifting bin 1010 is unnecessary to clear the front wall. In various embodiments, front wall 150 is not present at all. In various embodiments where the outside surface 116 and the bin 1010 have a coefficient of friction high enough to keep the bin 1010 from sliding, either because of the material used to create bottom panel 110 or because of a coating or covering on outside surface 116, the bin 1010 remains in position even where the inclination angle A1 is greater than zero and the angle A2 is zero or even negative.

In various embodiments where angle A2 is zero or negative and the combination of the material of bin 1010 and the material of bottom panel 110 may not have a high enough coefficient of friction to keep bin 1010 from sliding, an anti-friction material can be added. This anti-friction material can be made of a group of materials including, but not limited to the following: rubber, silicone, polymeric materials having sufficient anti-friction qualities, and materials having magnetic properties in combination with pans that are equally imbued. In various embodiments where the storage bin system 10 is transported on a piece of equipment that is mobile and therefore subject to acceleration, impact forces, vibration, or other kinds of movement or jostling, the rear wall 120, side walls 130,140 and front wall 150 are sufficiently able to keep bin 1010 in position so that bin 1010 does not fall from bin support 100. In various embodiments, the rear wall 120, side walls 130,140 and front wall 150 are sufficiently able to keep bins 1010 inside bin support 100 without dumping the contents of bins 1010 due to movement inside the bin support 100. In various embodiments where anti-friction materials are applied to the inside surface 115 or to the outside surface 116 or to a surface of bin 1010, storage bin system 10 is able to keep bin 1010 in place with or without a physical barrier such as front wall 150 extending vertically from the inside surface 115 of the bottom panel 110 of the bin support 100.

Figures 6, 7:
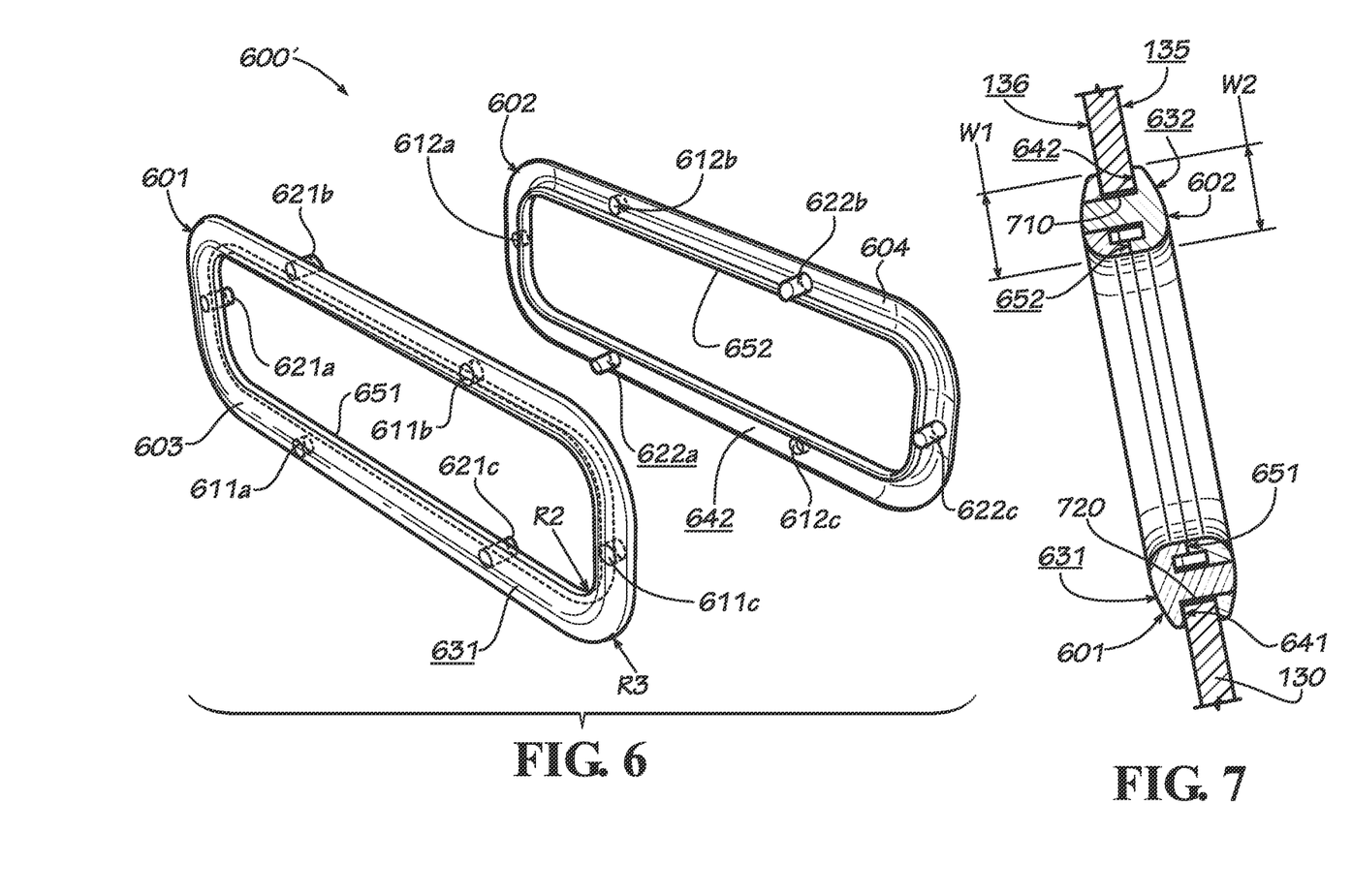
FIG. 6 is a perspective view of an embodiment of a pair of half inserts of another embodiment of the handle insert.
FIG. 7 is a sectional view of the handle insert of FIG. 6 installed in a handle cutout and taken along line 7-7 in FIG. 2 but incorporating features of the embodiment of the handle insert of FIG. 6.

In FIG. 2, handle insert 600a defines inside radius R2 and outside radius R3, where R2 and R3 are sized to define a constant outside trim width W1 for handle insert 600a,b. In various other embodiments, outside trim width W1 varies over the length of the handle insert 600a,b. In various other embodiments, outside trim width W1 and inside trim width W2 are substantially equal (as shown in FIG. 7). An inside trim width W2 (shown in FIG. 7) is defined by that portion of handle insert 600a,b that is exposed on the interior side of the bin support 100. In various embodiments, inside trim width W2 of handle insert 600a differs from outside trim width W1 (as shown in FIG. 1). In various embodiments, a user is able to more comfortably lift and otherwise handle storage bin system 10 when handle inserts 600a,b are present including when the storage bin system 10 is loaded. In various other embodiments, however, handle inserts 600a,b are not be present. In various embodiments, a single insert installed from one side may be used.

Figure 3:
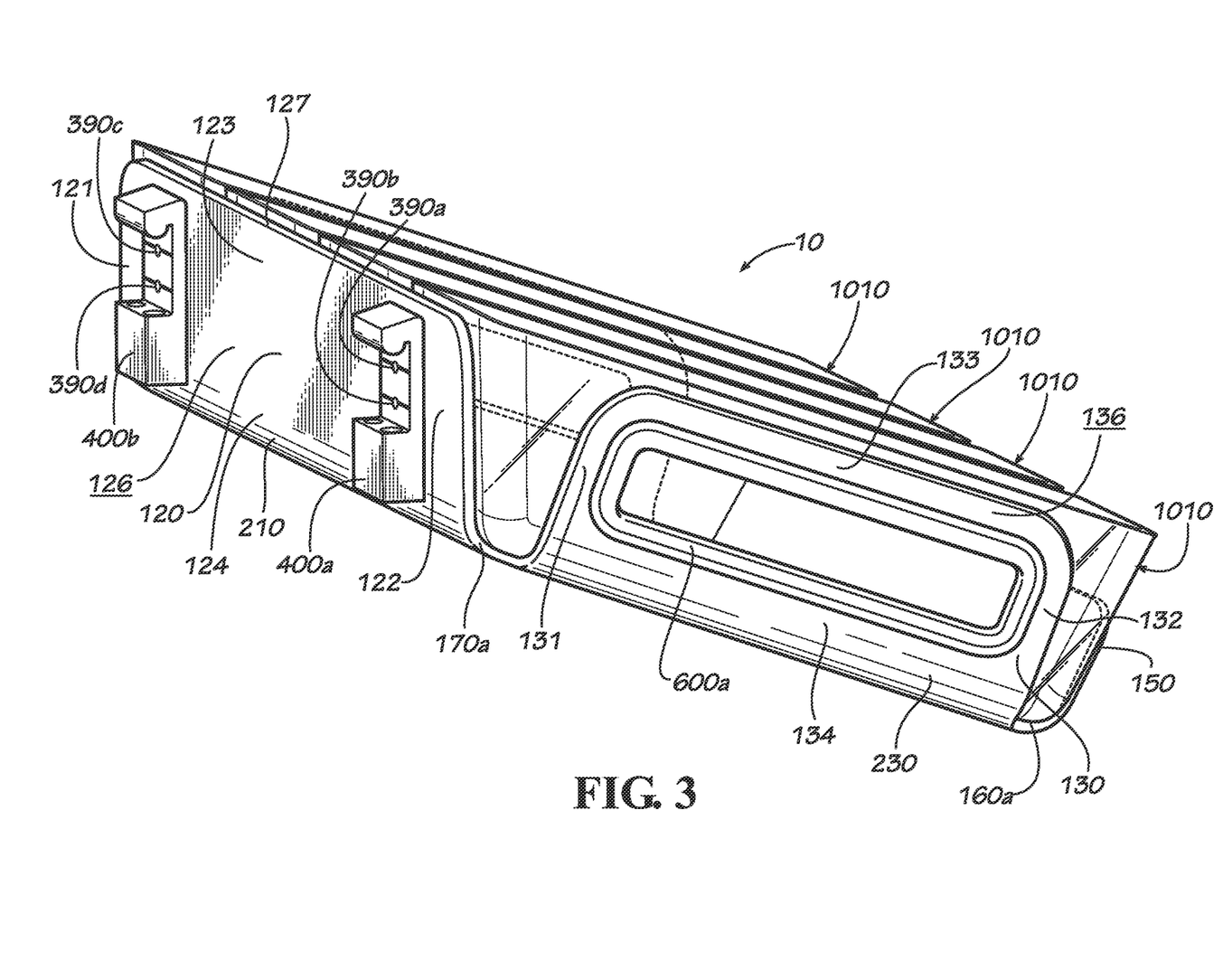
FIG. 3 is a perspective view of the storage bin system of FIG. 1 viewed from the rear.
Figure 4:
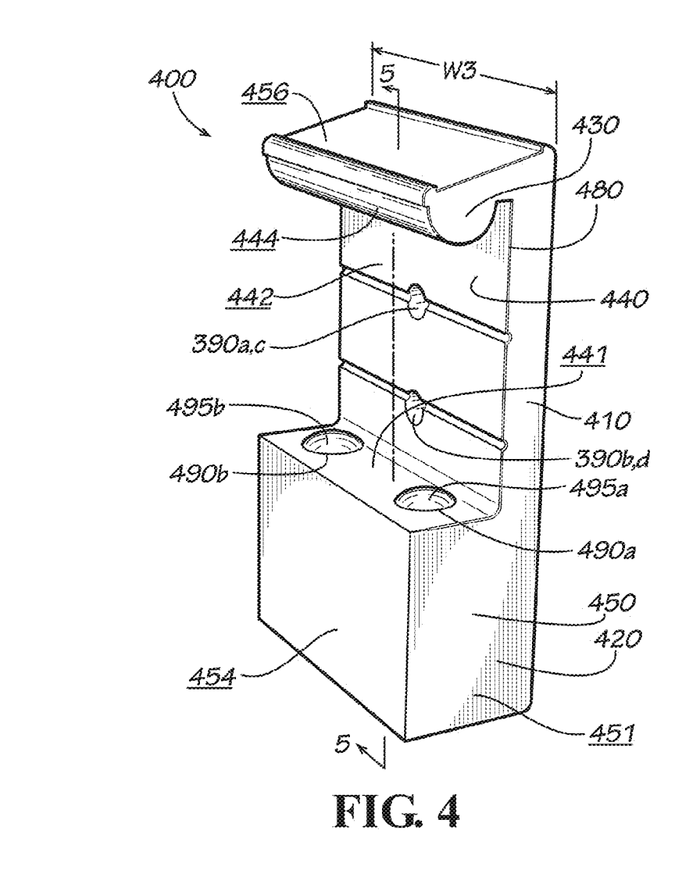
FIG. 4 is a perspective view of one embodiment of a rail adapter of the storage bin system of FIG. 1.

Disclosed in FIG. 3 is a perspective view of storage bin system 10 as viewed from the rear. Both rail adapter 400a and rail adapter 400b are visible as is the outside surface 126 of rear wall 120 to which rail adapters 400a,b are attached. As shown, rail adapter 400a defines mounting holes 390a,b and rail adapter 400b defines mounting holes 390c,d. Together with mounting holes 190a,b,c,d defined in rear wall 120, mounting holes 390a,b,c,d in rail adapters 400a,b are used in various embodiments to attach rail adapters 400a,b to rear wall 120. The detailed design of rail adapters 400a,b is shown in FIG. 4.

Figure 5:
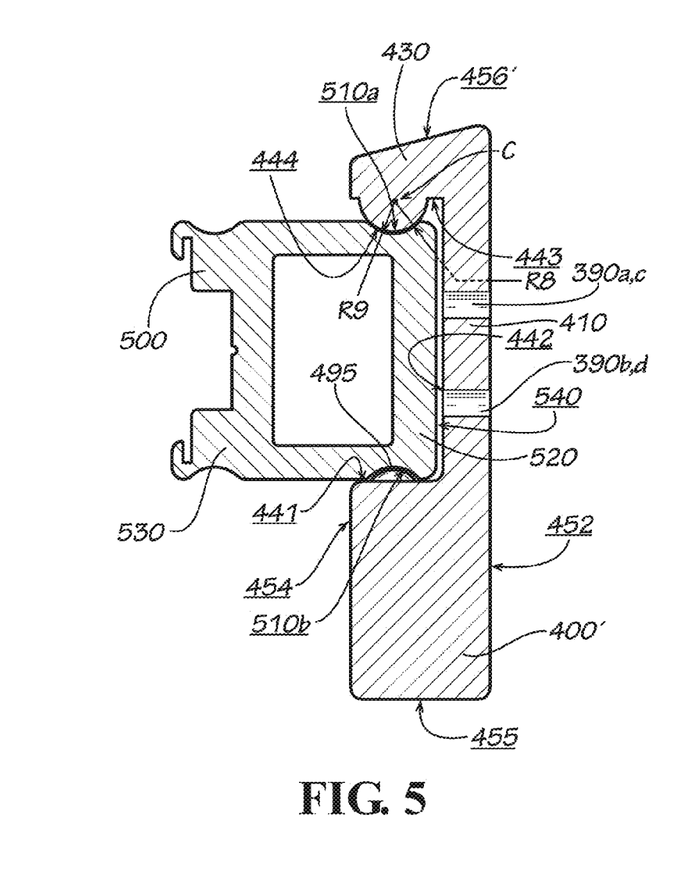
FIG. 5 is a sectional view of another embodiment of a rail adapter assembled with a rail member taken along line 5-5 in FIG. 4.

Rail adapter 400 includes a middle portion 410, a lower portion 420, and an upper portion 430. Rail adapter 400 defines an internal cavity 440 and an exterior surface 450 allowing rail adapter 400 to engage with any number of different rails (an embodiment of which is shown in FIG. 5). In various embodiments, internal cavity 440 includes a horizontal surface 441, a vertical surface 442, a horizontal surface 443 (shown in FIG. 5), and an engagement surface 444. In addition to internal cavity 440, the exterior 450 of rail adapter 400 includes a pair of opposing end surfaces including a first surface 451 and a second end surface (not shown) distal from end surface 451; a mounting surface 452 (shown in FIG. 5) for mounting rail adapter 400 to bin support 100; an outside surface 454, a bottom surface 455 (shown in FIG. 5), and a top surface 456. In various embodiments, the intersection between surfaces is eased by edge relief 480 including radiused sections or flat sections (such as a chamfer) or a combination of both radiused and flat sections.

In various embodiments, rail adapter 400 includes vertical bores 490a,b for receiving one or more ball detent mechanisms 495. In the current embodiment, there are two ball detent mechanisms 495a,b, though any number of ball detent mechanisms 495 may be present in various embodiments, including zero, one, or three or more ball detent mechanisms 495. In various embodiments, ball detent mechanisms 495a,b help positively fix rail adapter 400 onto rail member 500 but also facilitate removal once a minimum force is applied, where typically the minimum force is that lateral force away from the rail that will result in a normal force on the ball of ball detent mechanism 495 that is sufficient to push the outermost surface of the protruding ball towards horizontal surface 441 of internal cavity 440 of rail adapter 400. In various embodiments, a ball detent spring may further be included with each ball detent mechanism 495a,b in its respective bore 490a,b to bias the ball detent mechanism 495 against the rail member 500 within engagement surface 510b. In various embodiments, the vertical bore 490a,b for each ball detent mechanism 495a,b may or may not pass completely through the rail adapter 400 and may include a plug such as a screw or bolt within each vertical bore 490a,b to hold each ball detent mechanism 495a,b and the ball detent spring within the respective vertical bore 490a,b.

In various embodiments, rail adapter 400 may include another vertical bore in addition to vertical bores 490a,b for receiving a fastener (not shown) for securing rail adapter 400 to rail member 500 or equivalent so that rail adapter 400 cannot slide longitudinally along the rail member 400. In various embodiments, the vertical bore may include threaded portions (not shown) to facilitate the use of the aforementioned fasteners.

Rail adapter 400 has width W3, which is measured in a plane parallel to mounting surface 452. In various embodiments, two or more rail adapters with a relatively small value for width W3 secures the bin support 100 to the rail. In various embodiments, only one rail adapter 400 is required, with a width W3 sufficiently able to secure the bin support 100 to the rail (not shown) without bin support 100 being able to rotate excessively or at all. In various other embodiments, rail adapters are not required to secure the bin support 100 to the rail where rear wall 120 is adapted to accomplish the same purpose. In various embodiments, for example, rear wall 120 includes an additional leg bending downward and away from bin support 100, the leg able to hook or otherwise secure onto a rail without rail adapters 400. In various embodiments, rail adapters 400 are not required because the bin support 100, instead of being suspended from one end, is placed on top of a surface that provides the necessary support through the use of a wedge (not shown) or other structure (as is described below).

FIG. 5 shows a sectional view of the interaction between a rail adapter 400' and a rail member 500 as viewed from the side. One difference between rail adapter 400 and rail adapter 400' is the contour or shape of a top surface 456' as compared to that of top surface 456. The top surface 456' of rail adapter 400' is substantially flat while a middle portion of the top surface 456 of rail adapter 400 is recessed. Rail member 500 includes a first engagement end 530 and a second engagement end 520. In various embodiments, the first engagement end 530 of rail member 500 is mountable on any one of a number of structures. Engagement surface 444 of rail adapter 400' is shown in engagement with an engagement surface 510a of rail member 500 such that rail adapter 400' is not separable from rail member 500 except by rotating rail adapter 400' about center point C of upper portion 430 far enough for outside surface 454 of rail adapter 400' to clear vertical surface 540 of rail member 500 so that engagement surface 444 and engagement surface 510a can be separated and the rail adapter 400' (and that which is attached thereto) can be removed from the second engagement end 520 of rail member 500. In various embodiments, engagement surface 444 includes an arcuate portion with radius R8. In various embodiments, engagement surface 510a includes an arcuate portion with radius R9. In various embodiments, radius R8 and radius R9 are equal in magnitude. Also disclosed in FIG. 5 is the engagement surface 510b, which is opposite engagement surface 510a at the second engagement end 520 of rail member 500. In various embodiments including ball detent mechanisms 495a,b, engagement surface 510b engages ball detent mechanisms 495a,b to attach the rail adapter 400 with the rail member 500. In various embodiments, the presence of engagement surface 510b allows rail member 500 to be rotated 180 degrees and serve the same function as engagement surface 510a. It also allows a rail adapter 400 that is mounted on a vertically-oriented rail member 500 to be mounted to the left or to right of that vertically-oriented rail member 500. In various embodiments making use of a rail member 500 that is vertically-oriented, the rail adapter 400 is rotated ninety degrees with respect to the bin support 100 so that the bin support 100 remains level from the first side wall 130 to the second side wall 140 facing the front wall 150.

FIG. 6 discloses a second embodiment of a pair of half inserts 601,602 of a handle insert 600'. In various embodiments, handle insert 600' is described as liner 600' or handle liner 600' or vice versa. Half insert 601 includes a frame 603, a plurality of holes 611a,b,c defined in frame 603, and a plurality of pins 621a,b,c. Half insert 602 includes a frame 604, a plurality of holes 612a,b,c defined in frame 604, and a plurality of pins 622a,b,c. Frame 603 includes a flange 651 and defines an outer surface 631 and an inner surface 641 (shown in FIG. 7). Frame 604 includes a flange 652 and defines an outer surface 632 (shown in FIG. 7) and an inner surface 642. In various embodiments, half insert 601 and half insert 602 include identical geometry and engage with each other to create the handle insert 600'. In order to engage half insert 601 with half insert 602, pins 621*a,b,c* of half insert 601 are inserted into holes 612*a,b,c*, respectively, of half insert 602, and pins 622*a,b,c* of half insert 602 are inserted into holes 611*a,b,c*, respectively, of half insert 601. Holes 611*a, b,c* of half insert 601 and holes 612*a,b,c*, of half insert 602 are shown as being defined through the entire thickness of frame 603 and frame 604, respectively; and pins 621 *a,b,c* of half insert 601 and pins 622*a,b,c* of half insert 602 are shown as being long enough to protrude completely through frame 603 and frame 604, respectively, so that the axial end of each pin 621,622 that is distal to frames 603,604, respectively, is substantially flush with the outer surfaces 631,632 of frames 603,604, respectively. In various embodiments, inner surfaces 641,642 are flat and outer surfaces 631,632 are rounded.

FIG. 7 is a sectional view of handle insert 600' replacing handle insert 600 in handle cutout 138 (shown in FIG. 1) defined by the first side wall 130 of bin support 100. A plurality of holes 710 and holes 720 defined in the first side wall 130 are sized and located to accept pins 621,622 of half inserts 601,602, respectively. Having completed the installation of handle insert 600', inner surface 642 of half insert 602 is shown in mating contact with inside surface 135 of first side wall 130. Similarly, inner surface 641 of half insert 601 is shown in mating contact with outside surface 136 of first side wall 130. This arrangement brings the opposing surfaces of flange 651 of half insert 601 into mating contact with flange 652 of half insert 602. Once installation is complete, no crevices or gaps remain in handle insert 600' or between handle insert 600' and first side wall 130. In various embodiments, adhesive is used to fixably attach handle insert 600'. In various other embodiments, adhesive is not required to fixably attach handle insert 600'.

In various embodiments, holes 611*a,b,c* of half insert 601 and holes 612*a,b,c*, of half insert 602 do not extend through and be defined by outer surface 631 of half insert 601 and outer surface 632 of half insert 602 but are "blind holes" that extend only partially through frames 603,604 such that pins 621*a,b,c* of half insert 601 and pins 622*a,b,c* of half insert 602, shortened as necessary, are covered from view once installation of the handle insert 600' is complete. In various embodiments, hiding the pins 621,622 facilitates cleaning and reduce the risk of accumulation of foreign substances on the handle insert 600', which is susceptible to soiling in various embodiments where personnel, with or without gloves, are able to unintentionally soil parts of the storage bin system 10—including handle inserts 600—with foreign substances including bio-hazardous substances which may harbor various bacteria or viruses having the potential to transmit communicable diseases.

In various embodiments, handle insert 600,600' or portions thereof are formed from any one or more of a number of metallic, rubber, polymeric, or other non-metallic materials including, but not limited to, natural or synthetic rubbers, acetal (such as DELRIN), polyamide (such as NYLON), and polyvinylchloride (PVC). In various embodiments, the durometer or hardness of different portions of the handle insert 600,600' varies. In various embodiments, portions of the handle requiring strength and rigidity use a material having a higher durometer for improved reliability while portions of the handle to be directly gripped by the user use a material having a lower durometer for improved ergonomics. In various embodiments, handle insert 600,600' is formed from one piece of elastomeric material like the structure and material of a grommet used for edge protection in a cutout through sheet metal.

Figure 8:
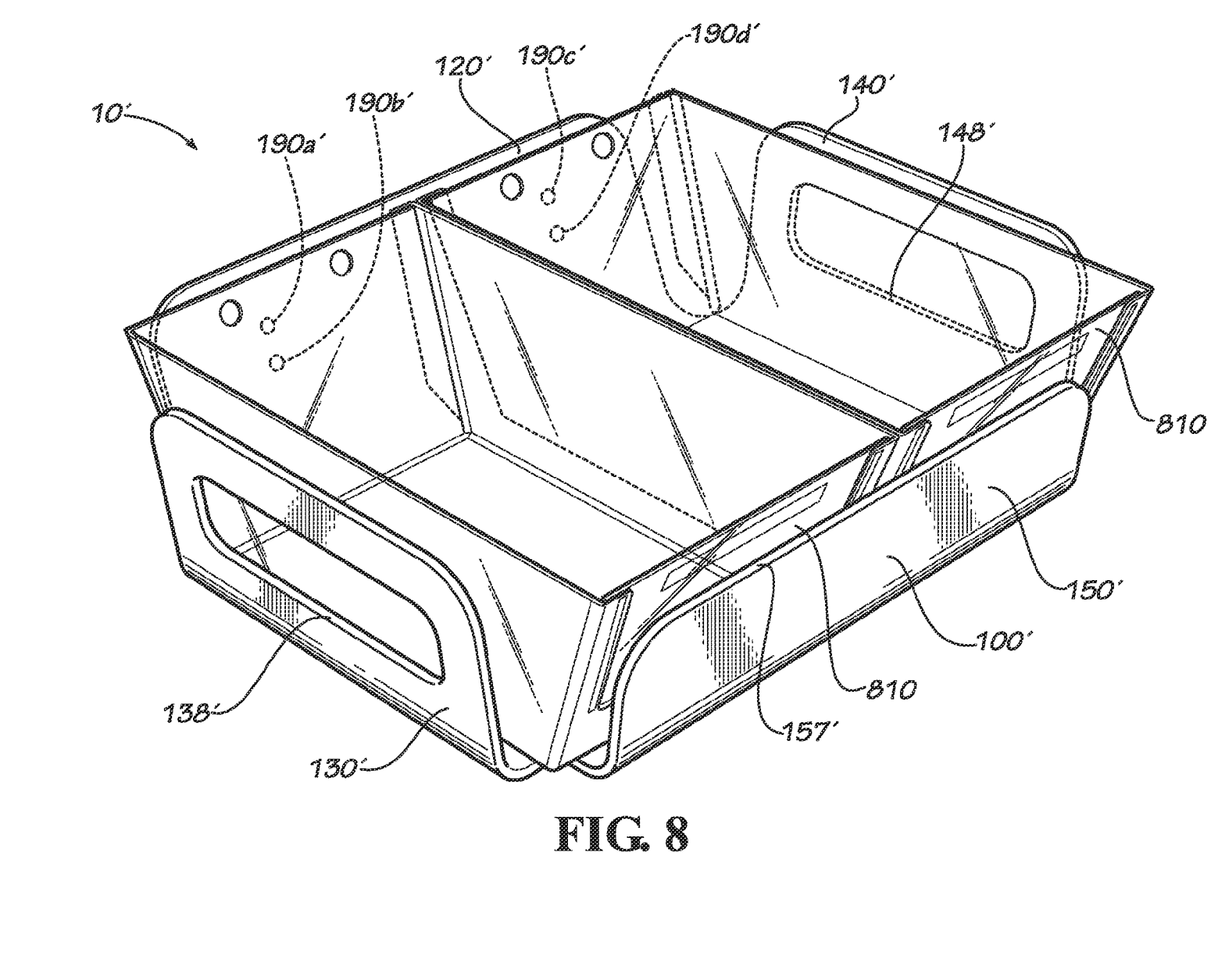
FIG. 8 is a perspective view of another embodiment of a storage bin system.

FIG. 8 discloses a second embodiment of a storage bin system 10'. Storage bin system 10' includes bin support 100', a plurality of bins 810, and a pair of rail adapters (not shown) mounted to rear wall 120' of bin support 100' using mounting holes 190*a'*, 190*b'*, 190*c'*, and 190*d'* defined in bin support 100'. In addition to rear wall 120', bin support 100' also includes a bottom panel (not shown), a first side wall 130', a second side wall 140', and a front wall 150'. First side wall 130' defines a handle cutout 138', and second side wall 140' defines a handle cutout 148'. In various embodiments, a handle insert is not a required part of bin support 100' because handle cutouts 138', 148' are sufficiently smooth. In various embodiments, each edge of handle cutouts 138', 148' may be chamfered or radiused to improve the safety or comfort of the handle cutouts 138', 148' during use.

Figure 9A:
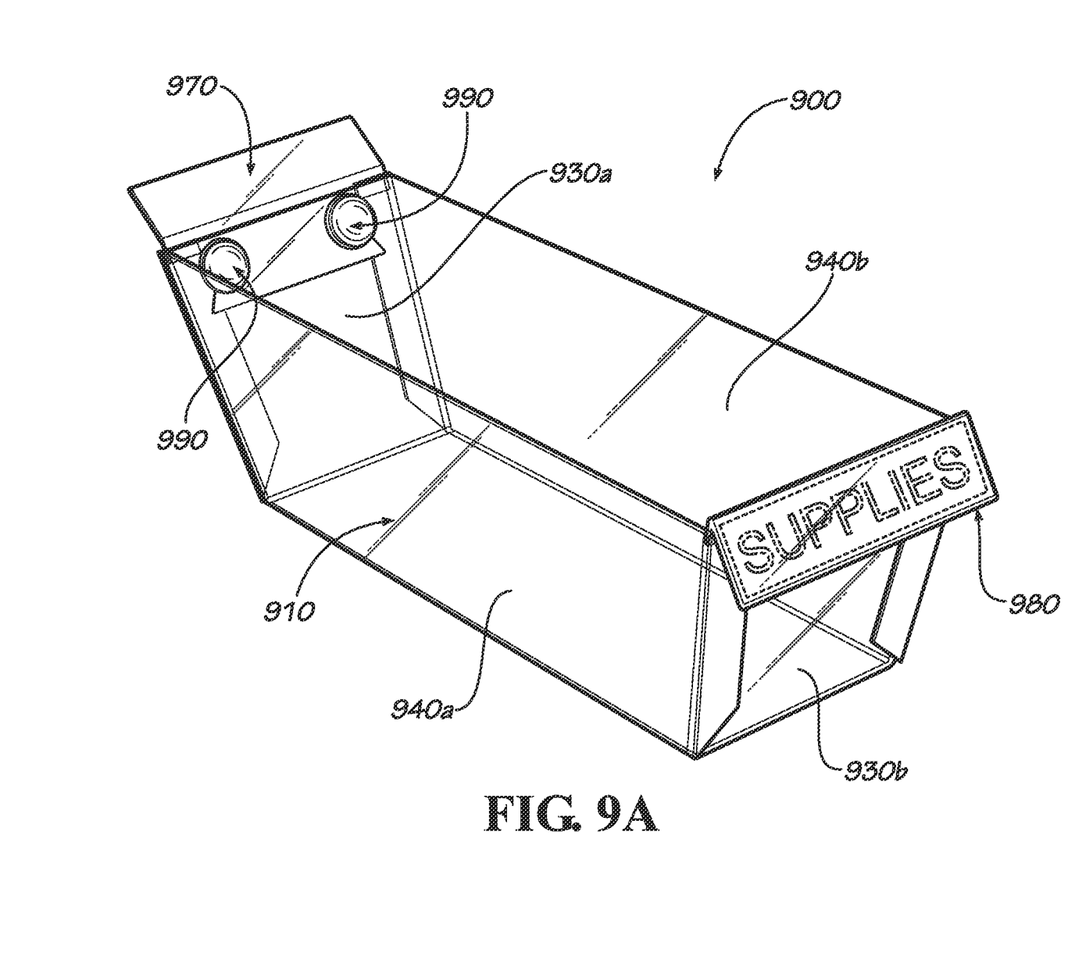
FIG. 9A is a perspective view of one embodiment of an accessorized bin.

FIG. 9A discloses one embodiment of an accessorized bin 900 including bin 910, label holder 970, label holder 980, and fasteners 990 for securing label holders 970,980 to bin 910. Bin 910 includes side walls 940*a,b* and end walls 930*a,b* to which label holders 970,980 are attached. In various embodiments, fasteners 990 are snap-in rivets that are assembled through one or more mounting holes 950 in bin 910. In various embodiments, fasteners 990 are formed from a polymeric material, although the disclosure of a polymeric material for fasteners 990 should not be considered limiting. In various embodiments, attachment of label holder 970 and label holder 980 to bin 910 is accomplished without the use of fasteners 990 for lower cost and improved cleanability in various embodiments. In various embodiments, label holders are formed as integral parts of one or more bins 910 or the equivalent.

In various embodiments, bin 910 is molded or stamped into a single continuous container by use of one or more of a group of molding processes including, but not limited to, thermoforming, vacuum forming, and injection molding, the result being no visible joints or gaps in bin 910 in various embodiments. In various other embodiments, bin 910 is fabricated from a flat blank (not shown) by folding various surfaces on the flattened blank into their final positions. In various embodiments, the areas of the die-cut blank where folds are subsequently made are thermally scored or otherwise weakened so that bins 910 after bending are substantially consistent in size and shape and to facilitate manufacturing in various embodiments. In various embodiments, a set of four scores around the bottom of each bin 910 receive a double score to help keep the sides of bin 910 straight. In various embodiments using the latter method of manufacture, joints or gaps may be visible. In various embodiments when bin 910 is fabricated from a flat blank, ultrasonic welding may be used to fixably attach the surfaces of the blank to each other to form the resulting three-dimensional container. In various embodiments, bins 910 are formed in such a way as to facilitate stacking of one bin 910 into another bin 910. In various embodiments, stacking will be possible for empty bins and for bins that are stocked with supplies. In various embodiments, stacking is facilitated by the incorporation of a draft angle on the sides of bins 910 as shown. In various other embodiments, a draft angle is not required or stacking is not required.

In various embodiments, bin 810, bin 910, bin 1010, and bin 1110 are made from a group of materials including, but not limited to metals, polymers, and papers. In various embodiments, bin 810, bin 910, bin 1010, and bin 1110 are made from a group of polymeric materials including, but not limited to, polypropylene (PP), polyethylene (PE) including high-density polyethylene (HDPE) and low-density polyethylene (LDPE), and polyethylene terephthalate (PET) among others. In various embodiments, the material used to make the bins 910 includes recycled material in whole or in part. In various other embodiments, the material used to make the bins 910 is non-recycled, or virgin, material. In various embodiments, the material is die cut from sheet material having an approximate thickness of 0.030 inches, but in various other embodiments the thickness is not 0.030 inches, and the disclosure of a 0.030 inch-thick material should not be considered limiting on the present disclosure.

Figure 9B:
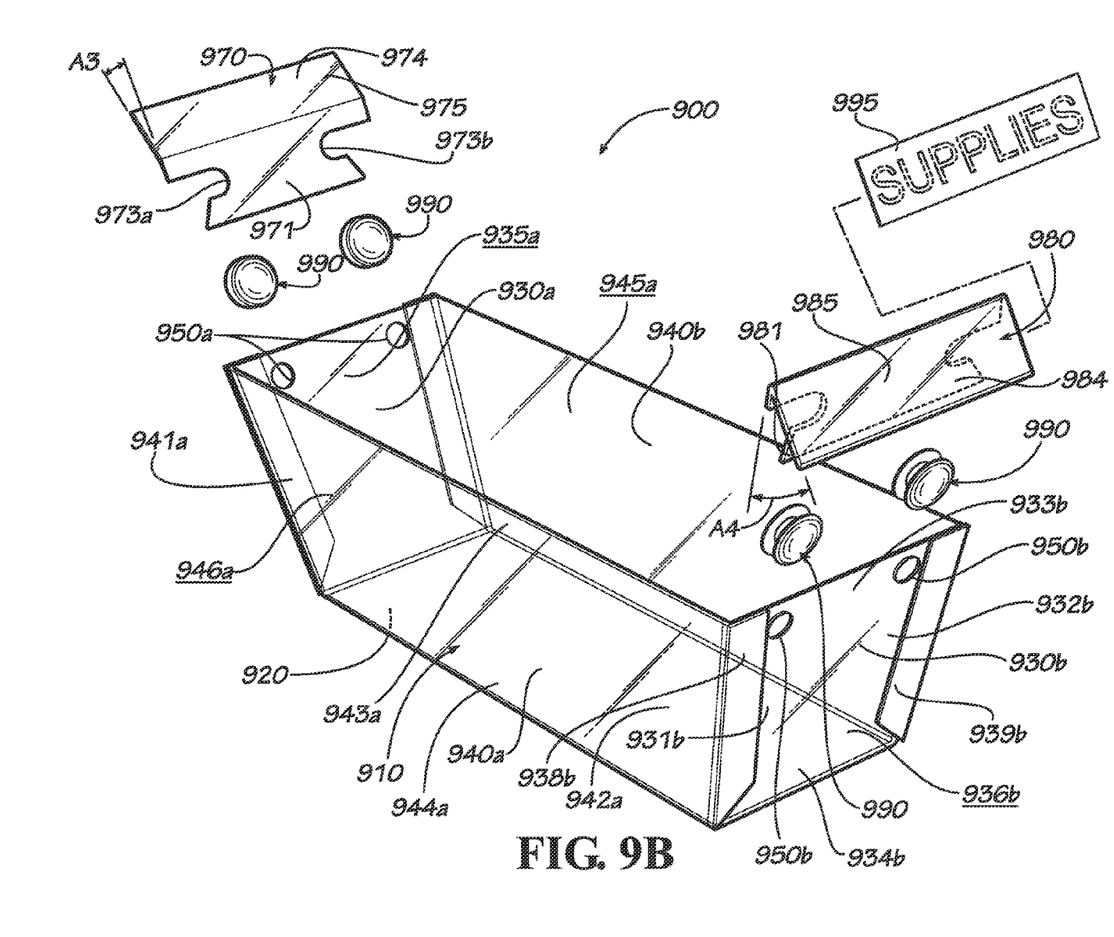
FIG. 9B is an exploded view of the accessorized bin of FIG. 9A.

FIG. 9B discloses an exploded view of the accessorized bin 900 in FIG. 9A. Bin 910 includes bottom 920, the aforementioned side walls 940a,b, and the aforementioned end walls 930a,b. Side wall 940a includes a first end 941a, a second end 942a, a top end 943a, and a bottom end 944a. In addition, side wall 940a defines an inside surface 945a and an outside surface 946a. Similarly, side wall 940b includes a first end 941b, a second end 942b, a top end 943b, and a bottom end 944b. In addition, side wall 940b defines an inside surface 945b and an outside surface 946b. End wall 930a includes a first end 931a, a second end 932a, a top end 933a, and a bottom end 934a. In addition, end wall 930a defines an inside surface 935a, an outside surface 936a, and mounting holes 950a for mounting label holder 970 or label holder 980 to end wall 930a. End wall 930b includes a first end 931b, a second end 932b, a top end 933b, and a bottom end 934b. In addition, end wall 930b defines an inside surface 935b, an outside surface 936b, and mounting holes 950b for mounting label holder 970 or label holder 980 to end wall 930b. In various embodiments, one of the end walls 930a,b or side walls 940a,b includes a tab 938a,b or a tab 939a,b that is bent to an angle of approximately ninety degrees relative to side walls 940a or 940b (as shown in FIGS. 9A and 9B) or relative to end walls 930a or 930b (not shown). In various embodiments, the aforementioned joining method of ultrasonic welding is used to secure tabs 938a,b and tabs 939a,b to the adjacent side walls 940a,b or end walls 930a,b. In various embodiments where the bins 910 are made from paper, joints are secured by use of an adhesive or simply by the paper itself through an inter-locking arrangement. In various embodiments where the bins 910 are made from metal, joints can be secured by welding. In various embodiments where a variation of bin (not shown) is made from metal, joints are left open similarly to the open corners of bin support 100 described herein.

In various embodiments, mounting holes 950a,b are circular in shape and are defined through the entire thickness of end walls 930a,b, respectively (including inside surfaces 935a,b and outside surfaces 936a,b, respectively). In various other embodiments, mounting holes 950a,b are not circular in shape. In various embodiments, label holder 970 and label holder 980 attach to bin 910 without the need for holes or fasteners. In various embodiments, label holder 970 includes shank 971 and flag 974. Shank 971 defines notches 973a,b for attaching label holder 970 to bin 910 by aligning mounting holes 950a with notches 973a,b and then installing fasteners 990 through both label holder 970 and bin 910. Flag 974 includes front 975 and rear 976. In various embodiments including where flag 974 is made from a translucent material, a label 995 is used for identification of the contents of the bin 910. In various embodiments, the label 995 is inserted between front 975 and rear (not shown) of flag 974 so that the label is visible through front 975. In various other embodiments, irrespective of the material from which flag 974 is made, a label 995 is affixed to an outside surface of front 975 of flag 974 so that the label is visible through front 975. At least partly to facilitate easier viewing of any label (not shown) affixed to label holder 970, flag 974 of label holder 970 is shown angled away from the plane occupied by shank 971 by an angle A3 shown. In various embodiments, some labels are of a different color than other labels to facilitate color coding for improved organization, efficiency, or safety. In various embodiments, labels 995 are made from a paper material, although the disclosure of a paper label should not be considered limiting.

In various embodiments, label holder 980 includes shank 981 and flag 984. Shank 981 defines notches 983a,b (similar to notches 973a,b of shank 971 but not shown) for attaching label holder 980 to bin 910 by aligning mounting holes 950b with notches 983a,b and then installing fasteners 990 through both label holder 980 and bin 910. At least partly to facilitate easier viewing of any label affixed to label holder 980, flag 984 of label holder 980 is shown angled away from the plane occupied by shank 981 by an angle A4 shown. In various embodiments, angle A4 as shown results in flag 984 being bent downwards, or alternately, a distal portion of flag 984 pointing downwards.

In various embodiments, the accessorized bin 900 or bin 910 is marked with graphics or text by applying a chemical such as ink to a surface of a side of the bin 910—for example, to end wall 930b—to identify the manufacturer of the bin 910 by its name or logo, the intended content of the bin 910, a graphic representing a particular recycling code or symbol, or other important information. In various embodiments, the bins 910 are marked with graphics or text by thermal embossing of the material or other forming of portions of the bin 910 into the shape of the graphics or text. In various embodiments, the label 995 is inserted into a pocket or sleeve in end wall 930a or end wall 930b or affixed to an outside or inside surface of the bin 910 without the need for a separate label holder.

Disclosed in FIG. 10 and referenced in the description of the other figures is a front view of another embodiment of a storage bin system 10" including bin support 100" and a plurality of bins 1110. The first side wall 130 and the second side wall 140 are shown angled outward at angle A5. Bins 1110 are shown with bin draft angle A6 that in various embodiments matches angle A5. In various embodiments, clearance width W4 shown on each side of storage bin system 10" provides space as needed for a user to grip hand holds on each side of the storage bin system 10" with his or her hands. This is beneficial in various embodiments where side wall vertical height H2 is lower than overall height H3, which is the height of the storage bin system 10" with bins 1110 installed. Previously mentioned radii R6, R7 are also shown as well as transition portion 230 shown at the intersection between the first side wall 130 and the bottom panel 110 and also transition portion 240 shown at the intersection between the second side wall 140 and the bottom panel 110.

Also disclosed is a method of installing the storage bin system 10,10' including: connecting a rail adapter 400,400' to a bin support 100,100'; and hanging the bin support 100,100' on a rail member 500 by connecting the rail adapter 400,400' to the rail member 500. As previously described, detachment of the bin support 100,100' from rail member 500 engagement surface 444 of rail adapter 400,400' is accomplished in various embodiments by rotating the lower portion 420 of rail adapter 400' about center point C of upper portion 430 enough for outside surface 454 of rail adapter 400' to clear vertical surface 540 of rail member 500 so that engagement surface 444 and engagement surface 510a can be separated and the rail adapter 400' (and that which it attached thereto) can be removed from the second engagement end 520 of rail member 500. Installation of the bin support 100,100' on rail member 500 involves positioning engagement surface 444 of rail adapter 400,400' above engagement surface 510a of rail member 500, rotating the lower portion 420 of rail adapter 400,400' about center point C of upper portion 430 enough for vertical surface 442 of rail adapter 400, 400' to become substantially parallel to vertical surface 540 of rail member 500.

In various embodiments, the storage bin system 10 includes the step of simultaneously removing the rail adapter (if present), the bin support 100, and bins 1010 from the rail as a system. In various embodiments, partially-depleted storage bin systems 10 are removed from a vacated room and transported on the "unclean" side of a supply cart (not shown). This can be described as a "substitution system" of materials handling. In various embodiments, each set of bins 1010 may be filled or one or more individual bins 1010 replaced piecemeal from a central supply. The storage bin system 10 is able to be used, refilled, and transferred in these and a variety of other ways. In various embodiments, bins 1010 are sealed with plastic foil or with lids or covers having hinged or non-hinged features as desired so as to keep out contamination in various embodiments. In various other embodiments, such care to seal the contents of the bins 1010 need not be taken.

In this regard, the present disclosure provides a storage bin system 10 that is configured and arranged for mounting onto a hospital rail system using a standardized rail adapter mount. The bin support 100 is formed from a solid sheet, like a tray, with turned-up edges. In various embodiments, the turned-up edges serve as handles. In various embodiments, the turned-up edges are side walls 130,140. In various embodiments, the turned-up edges include hand holes which in various embodiments have liners installed therein. In various embodiments, the liners are handle inserts 600. In various embodiments, the bin support 100 is inclined downwards towards the front to create a display for the stored items. The stock that is stored in the bins 1010 can be seen from across the room and also physically reached equally well by tall and short personnel. This is important because supply management relies on having the minimum of supplies in each room, but never too few items. Visually checking the inventory is important. In various embodiments, storage bin system 10 is flexible enough to neatly store multiple items even when those items are of different sizes and shapes. In various embodiments with multiple bins 1010 or the equivalent, items are stored separately to keep the items separately organized.

The bin support 100 holds bins 1010 and supports them from a standard hospital rail such as rail member 500. Preferably clear bins are employed in lieu of partitions. Using separate bins 1010 instead of one large container with partitions, an individual bin 1010 can be taken off the bin support 100 with all its contents. The bin 1010 can be removed for refilling, replacing, cleaning or if needed in a work area. Furthermore, the bins 1010 are interchangeable in various combinations and positions such that one, two, three, four (as shown in various figures) or five or more bins of various sizes and shapes are able to completely fill a bin support 100 from side to side. In addition, portions of bins or combinations thereof can be used with storage bin system 10.

In contrast to the wire baskets in the prior art, the easy-to-clean surfaces of the bin support 100 can be wiped off. Any accumulated debris can be maneuvered into the cutouts 160a,b at the front corners and cutouts 170a,b at the rear corners as needed for collection, and there are no crevices to catch residual debris. The bins 1010 are removable and replaceable and can also easily be cleaned.

Because the structure of the bin support structure 100 is stiff, the rail mounting adapters near each end work in sync, and the bin support is easy to hang on or remove from a hospital accessory rail such as rail member 500. Further, a pair of wedges (not shown) can be attached to the underside of the bin support 100 so that the bin support 100 can be removed from an accessory rail such as rail member 500 and be set on a flat surface while maintaining its inclination.

In various embodiments, bin support 100,100',100" or the storage bin system 10,10',10" of which bin support 100,100', 100" is a component in various embodiments is supported on a structure. In various embodiments, a structure is either a stationary structure or a mobile structure. The structure may be a support platform in various embodiments. Examples of stationary structures include, but are not limited to, a mounting member such as rail member 500, other rails, walls, headwalls, ceiling-mounted or wall-mounted booms from various manufacturers, free-standing and/or movable columns and other structures typically found in hospital rooms and treatment facilities to which a rail 500 or rail member 500 may be attached. Examples of mobile structures include, but are not limited to, supply carts, patient beds, gurneys, wheelchairs, ambulances, helicopters, and other vehicles and mobile platforms and any of the surfaces found therein or thereon. However, the disclosure of these specific examples of structures should not be considered limiting.

These together with other objects of the disclosure, along with various features of novelty that characterize the disclosed storage bin systems 10, are pointed out with particularity in the further description annexed hereto and forming a part of this disclosure. For a better understanding of the disclosed storage bin system 10, its operating advantages and the specific objects attained by its uses, reference should be had to the accompanying drawings and descriptive matter in which there is illustrated several exemplary embodiments of the disclosed storage bin system 10.

One should note that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment.

It should be emphasized that the above-described embodiments are merely possible examples of implementations, merely set forth for a clear understanding of the principles of the present disclosure. Any process descriptions or blocks in flow diagrams should be understood as representing modules, segments, or portions of code which include one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, That which is claimed is:

1. A storage bin apparatus comprising:
a bin support configured to store bins and items, the bin support including a bottom panel, a front stop, a rear wall, and side walls, wherein the sidewalls, the bottom panel, the rear wall and the front stop define cutouts at each corner of the bin support, wherein a handle cutout opening configured to receive a hand is formed within at least one of the sidewalls, and a handle insert is attached along the handle cutout opening, wherein the handle insert includes a first half insert and a second half insert, each of the first half insert and the second half insert comprising a frame, the frame of each of the first half insert and the second half insert comprising a plurality of pins protruding from the frame and defining a plurality of holes; the second half insert is fixably attached to the first half insert through the handle cutout opening, the plurality of pins of the first half insert received within the plurality of holes of the second half insert and the plurality of pins of the second half insert received within the plurality of holes of the first half insert; and
a mounting adapter comprising a lower portion, a middle portion, and an upper portion; the mounting adapter defining a mounting surface and an internal cavity distal from the mounting surface, the internal cavity defining a horizontal surface and an engagement surface opposite from the horizontal surface; a ball detent mechanism assembled in a vertical bore defined in the horizontal surface, a ball of the ball detent mechanism protruding from the horizontal surface; the mounting surface of the mounting adapter removably attached to the rear wall of the bin support at a connection point and extending from the connection point away from the front stop, the mounting adapter mountable to a horizontal mounting member, the internal cavity configured to receive the horizontal mounting member, wherein the horizontal mounting member is configured to be wedged between the ball of the ball detent mechanism and the engagement surface of the mounting adapter in order to suspend the bin support from a wall.

2. The apparatus of claim 1, wherein the bottom panel is inclined with respect to a horizontal plane when the rear wall is aligned with a vertical plane.

3. The apparatus of claim 1, wherein the mounting adapter is a rail adapter and the horizontal mounting member is a horizontal rail member.

4. The apparatus of claim 1, wherein the front stop is a front wall.

5. A storage bin system comprising:
a bin support configured to store bins and items, the bin support including a bottom panel, a front stop, a rear wall, and side walls; wherein a handle cutout opening configured to receive a hand is formed within at least one of the sidewalls, and a handle insert is attached along the handle cutout opening, wherein the handle insert includes a first half insert and a second half insert, each of the first half insert and the second half insert comprising a frame, the frame of each of the first half insert and the second half insert comprising a plurality of pins protruding from the frame and defining a plurality of holes; the second half insert is fixably attached to the first half insert through the handle cutout opening, the plurality of pins of the first half insert received within the plurality of holes of the second half insert and the plurality of pins of the second half insert received within the plurality of holes of the first half insert;
a rail adapter comprising a lower portion, a middle portion, and an upper portion; the rail adapter defining a mounting surface and an internal cavity distal from the mounting surface, the internal cavity defining a horizontal surface and an engagement surface opposite from the horizontal surface, the horizontal surface defined in the lower portion of the rail adapter and the engagement surface defined in the upper portion of the rail adapter, a ball detent mechanism protruding from a vertical bore defined in the horizontal surface; the mounting surface of the rail adapter attached to the rear wall of the bin support at a connection point and extending from the connection point away from the front stop;
a horizontal rail member inserted within internal cavity of the rail adapter so that the horizontal rail member is wedged between the engagement surface and the ball detent mechanism of the rail adapter in order to suspend the storage bin from a wall; and
a bin positioned on the bottom panel of the bin support.

6. The system of claim 5, wherein the bin is formed by folding a blank into a three-dimensional shape.

7. The system of claim 5, wherein the bin is made from a polymeric material.

8. The system of claim 5, wherein the bin support and the bin include only MRI-safe materials.

9. The system of claim 5 further comprising a label holder, the label holder adapted to receive a label.

10. The system of claim 5, wherein the side walls, bottom panel, and front stop define cutouts at front corners of the bin support.

11. The apparatus of claim 1, wherein the side walls comprise a first side wall and a second side wall, a second transition portion between the bottom panel and the first side wall defining a second radius, a third transition portion between the bottom panel and the second side wall defining a third radius, and a fourth transition portion between the bottom panel and the rear wall defining a fourth radius.

12. The apparatus of claim 1, further comprising the horizontal mounting member, wherein the horizontal mounting member is a rail member and the mounting adapter is a rail adapter; the rail adapter mounted on the rail member, the horizontal surface of the rail adapter defined in the lower portion of the rail adapter positioned below the rail member, and an engagement surface defined in an upper portion of the rail adapter positioned above the rail member.

13. The apparatus of claim 1, wherein the first radius measures a minimum of ¼ inch.

14. The apparatus of claim 1, wherein the first half insert and the second half insert include identical geometry.

15. The system of claim 5, wherein the rail member comprises a first engagement surface and a second engagement surface, and the first engagement surface comprising an arcuate portion; the engagement surface of the rail adapter engaged with the first engagement surface of the rail member and the ball of the ball detent mechanism engaged with the second engagement surface of the rail member to positively fix the rail adapter to the rail member.

16. The system of claim 5, wherein each of the bottom panel of the bin support and the bin include a material having magnetic properties.

* * * * *